Figure 1:
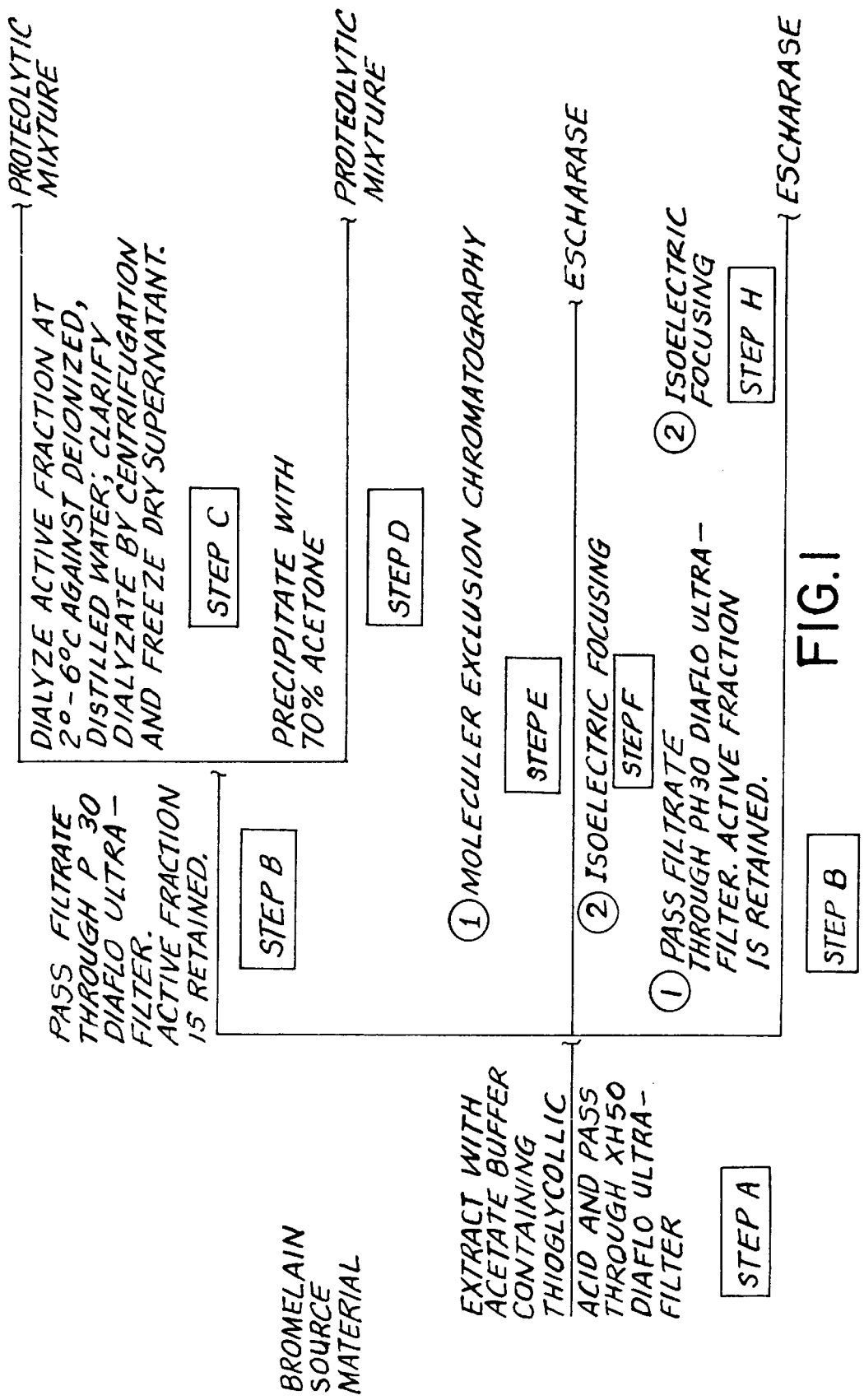

United States Patent [19]

Houck et al.

[11] Patent Number: 5,830,739
[45] Date of Patent: Nov. 3, 1998

[54] PROTEOLYTIC MIXTURE CONTAINING ESCHARASE AND METHOD OF ISOLATING SAME

[75] Inventors: John C. Houck, Seattle, Wash.; Gerold K. V. Klein, Brunswick, Me.

[73] Assignee: the estate of Gerold K.V. Klein, Brunswick, Me.

[21] Appl. No.: 337,318

[22] Filed: Nov. 10, 1994

Related U.S. Application Data

[63] Continuation of Ser. No. 208,035, Mar. 9, 1994, abandoned, which is a continuation of Ser. No. 985,235, Dec. 2, 1992, abandoned, which is a continuation-in-part of Ser. No. 801,968, Dec. 3, 1991, abandoned.

[51] Int. Cl.[6] .................................................... C12N 9/50
[52] U.S. Cl. ............... 435/219; 424/94.65; 424/DIG. 13
[58] Field of Search ...................... 424/94.65, DIG. 13; 435/219

[56] References Cited

U.S. PATENT DOCUMENTS

| | | | |
|---|---|---|---|
| 3,002,891 | 10/1961 | Heinieke | 435/219 |
| 3,817,834 | 6/1974 | Wilson | 435/219 |
| 4,197,291 | 4/1980 | Klein et al. | 424/94.65 |
| 4,226,854 | 10/1980 | Klein et al. | 424/94.65 |
| 4,307,081 | 12/1981 | Klein et al. | 424/94.65 |
| 4,329,430 | 5/1982 | Klein et al. | 435/219 |

FOREIGN PATENT DOCUMENTS 2 018 809   10/1979   United Kingdom .

OTHER PUBLICATIONS

Houck, et al., Isolation of An Effective Debriding Agent From The Stems of Pineapple Plants, Int. J. Tiss. Reac. V(2) 125–134 (1983).
Scopes, R. K., "Protein Purification", published 1982, pp. 43–52.
Rowan, et al. Ananain: A Novel Cysteine Proteinase Found in Pineapple Stem, published 1988, pp. 262–270.
Rowan, A. D., et al. "Debridement of Experimental Full–Thickness Skin Burns of Rats with Enzyme Fractions derived from Pineapple Stem", published 1990, pp. 243–246.
Scopes, R.K., Protein Purification, Second Edition, Springer Verlag, New York, 1987, pp. 33–64.

*Primary Examiner*—Jean C. Witz
*Attorney, Agent, or Firm*—George W. Neuner

[57] ABSTRACT

Method is described for obtaining a novel proteolytic mixture containing escharase from bromelain.

2 Claims, 1 Drawing Sheet

PROTEOLYTIC MIXTURE CONTAINING ESCHARASE AND METHOD OF ISOLATING SAME

This application is a continuation of Ser. No.: 08/208,035 Filed: Mar. 9, 1994, abandoned which is a continuation of Ser. No. 07/985,235 filed: Dec. 2, 1992, abandoned, which is a continuation-in-part of Ser. No. 07/801,968, filed Dec. 3, 1991, abandoned.

BACKGROUND OF THE INVENTION

Escharase is a hydrolytic enzyme material free of caseinolytic activity with an isoelectoic point of about six. It has a molecular weight of about 45,000 daltons and is comprised of three subunits believed to be identical, each weighing about 15,000 daltons.

Escharase and mixtures containing escharase are useful for the debridement of devitalized tissue from a mammalian host. It is particularly useful for the removal of devitalized tissue from human burn victims.

The product, methods of isolation and methods of use are well known and are described for example by Houck, Chang and Klein in Int. J. Tiss. Reac. V(2) 125–134 (1983) and in U.S. Pat. No. 4,197,291 issued Apr. 8, 1980; 4,226,854 issued Oct. 7, 1980 and 4,307,081 issued Dec. 22, 1981. All of these disclosures are incorporated herein in their entirety by reference.

The Houck et al publication and the patents describe methods of isolating escharase itself and a proteolytic mixture containing escharase by the procedures generally illustrated in FIG. 1 hereof. The proteolytic mixture containing the escharase and, of course, the escharase itself are useful for the debridement of devitalized tissue from mammals.

As will be seen from the figure, the first step in the isolation process is to extract commercially available bromelain with an acetate buffer containing thioglycollic acid and then to filter. Specifically, the commercial bromelain is extracted (10 grams per 200 ml) in acetate buffer 0.1M, pH 5.5 which has been made up to 1% in thioglycolic acid. The pH of this solution is approximately 4. The solution is expressed through XM 50 Amicon Diaflo ultrafilter (Amicon Corp., Boston, Mass.) and concentrated over PM 30 Diaflo filters. The active solution containing a mixture of proteolytic enzymes having molecular weights of from 30,000 to 50,000 dalton can be either dialyzed at 2° to 6° C. against deionized, distilled water (200 volumes), clarified by centrifugation, and the clear supernatant freeze dried; or the active fraction can be precipitated with 70% acetone. Both procedures produce useful proteolytic mixtures.

As shown in FIG. 1, escharase can be isolated from the proteolytic enzyme mixture obtained after expression through XM 50 Amicon Diaflo ultrafilter as described above.

In one isolation procedure, the enzyme mixture is subjected to molecular exclusion chromatography as a phenylmercuric salt [prepared by combining the mixture with an aqueous 0.2M citrate buffer saturated with the salt in accordance with the procedure of Ota et al in Biochem. 3:180 (1960)] on a column of Sephadex G 75. The elution of the escharase product from this column preceded the elution of pure stem bromelain, and therefore escharase must have a molecular weight in excess of bromelain, e.g. 32,000.

Sephadex G 75 is a polysaccharide gel available from Pharmacia of Upsala, Sweden. It is employed for molecular exclusion chromatography in accordance with procedures well known in the art.

The mixture obtained by exclusion chromatography is then fractionated by isoelectric focusing and subjected to polyacrylamide gel analytical eletrophoresis in 1% sodium diodecyl sulfate (SDS).

For isoelectric focusing, the mixture was mixed in a sucrose gradient with LKB Ampholine ampholytes initially from pH 3 to 10, and subsequently at pH 5–8. The active material was concentrated at a peak isoelectric point of pH 6.04, with a range from 5.85 to 6.12. This isoelectric point is markedly different from that described from bromelain (pH 4.7 and 9.9). See Vestberg Acta. Chem. Scand 20:820 (1966).

LKB Ampholine is available from the LKB Company of Sweden for isoelectric focusing. It is believed to be a mixture of small ampholytes.

The products isolated by isoelectric focusing have an extremely high order of escharase activity.

For further purification, the isoelectric focused, active material may be subjected to polyacrylamide gel electrophoresis at pH 9 in 1% (SDS) (Weber et al J. Viol. Chem 244:4406 (1969). Only one protein staining band can be visualized with a measured electrophoretic mobility which, when compared with standard proteins of known molecular weight, evidences a molecular weight of between 14,300 and 15,00 daltons. Since SDS is known to dissociate proteins into their various subunits if any, it is apparent that the escharase product of this invention comprises at least two, and most likely three subunits of substantially the same molecular weight.

The process of this invention makes available an improved proteolytic mixture containing much higher concentration of escharase. A particular advantage of the process of the invention is that it can be scaled up to use much larger quantities of the bromelain source. Moreover, it will consistently produce the same high yields.

As used in this description and claims, the term "bromelain" or "bromelain source" refers to any of a number of presently available bromelain preparations such as TMBC bromelain commercially available from Taiwan McKay. The bromelain is prepared from the stem of the pineapple plant. In the presently preferred procedure for obtaining bromelain for use in this invention, the juice from the stem is first adjusted to a pH of about 3 or 4 with phosphoric acid and, as described in the above identified patents and publication, sodium hydride or sodium sulfhydride is added to protect against sulfhydryl oxidation. The inert material is precipitated at about 30% acetone (addition of sufficient acetone so that the solution is 30% in acetone) and, after filtration, the clarified fluid is precipitated with 70% acetone. This precipitate is collected by centrifugation and either redissolved in water containing sodium hydride or sodium sulfhydride which has been acidified with phosphoric acid and reprecipitated, or dried in a vacuum oven directly. If the material is reprecipitated, 70% acetone is utilized. The dried material from either process is suitable as a starting material to obtain the products of this invention.

Dilute aqueous ascorbic acid refers to aqueous solutions containing from about 0.5 to 2% by weight ascorbic acid, preferably 0.75 to 1.25%, most preferably 1%.

Dilute aqueous ascorbic acid solutions are employed in the process of this invention to extract the bromelain source. The extract is clarified, for example by filtration and the proteolytic mixture containing the escharase is precipitated by the addition of ammonium sulfate. Typically, to achieve efficient precipitation sufficient ammonium sulfate is added to form at least a 30% solution by weight, although the amount employed may be sufficient to form a saturated solution. Typically the solution will be from about 35% to 45% by weight in ammonium sulfate.

The escharase containing proteolytic mixture of this invention may be obtained from the bromelain source described above by extraction with an aqueous medium containing a non-volatile antioxidant. It is isolated from the extract and may be further purified. In the presently preferred procedure, the bromelain source is extracted with an aqueous solution of ascorbic acid at a pH of from about 3 to 4 and the desired product precipitated from the extract with a precipitant such as ammonium sulfate. The precipitated proteolytic mixture may be used as such, but it is preferred to further purify the mixture and concentrate its escharase content.

A typical procedure for the isolation of a proteolytic mixture of this invention is as follows:

1. 1 kilo of bromelain is blended (Waring Blender) for 60 seconds in 10 liters of 1% ascorbic acid (10 mg/ml) in distilled water at 4°–10° C.
2. This suspension is adjusted with 4N HCl to pH 3.5–3.9.
3. The suspension is stirred at 4°–10° C. for 18 hours.
4. After separating the insoluble (20–25%) materials from the soluble fraction by filtration or centrifugation in the cold (4°–10° C.) the soluble fraction is made up to 40% saturation of ammonium sulfate (2842 gm/10 L) and allowed to stand at 4°–10° C. overnight.
5. After collecting the precipitate via centrifugation or filtration in the cold, the precipitate is dissolved in 10 liters of 0.3M acetic acid containing 0.1% ascorbic acid (1 mg/ml) in the cold (pH 3.0).
6. This extract is then washed with 40 liters of distilled water over a 10,000 Dalton hollow fiber ultra-filter using an Amicon DC-30 A system with filter membrane cartilage type H10P1020, DF-40. A flow rate of 300 to 400 ml/min. at 19–23 psi at 10° C. is maintained fro about two hours and the final volume is reduced to about 4.5 to 5.0 liters.
7. The resulting solution is then lyophilized and weighed, usually about 250 gm yield.

The process of this invention provides a much improved escharase containing proteolytic mixture compared to the proteolytic mixture obtained by the process of the patents and the publication. The mixture is obtained in much improved yields, for example about 25% yield.

Of special significance, is the fact that the proteolytic mixture of the invention contains from about 1% to 1.5% escharase by weight based on the total weight of the mixture. The previously described methods provided proteolytic mixtures which, on average, contained much smaller amounts of escharase. Moreover, the mixture is stable over a longer period of time and appears to produce consistently better graftable beds for the acceptance of new skin than could be obtained from the previously described procedures.

The mixture may be characterized as containing from about 1% to 1.5% escharase together with proteolytic enzymes from bromelain extractable with dilute aqueous ascorbic acid.

If desired, escharase can be isolated from the proteolytic mixture of the invention by the following procedure:

1. G-75 Sephadex column chromatography

Dissolve 4 to 7 gm of proteolytic mixture in 50ml of 0.3M acetic acid containing 1 mg/ml of ascorbic acid. After centrifugation at 1200–1500 g the clear fluid is subjected to exclusion column chromatography (G-75) and the biologically active (by bioassay) fraction behind the void column and in front of the major peak rich in general protease activity (assayed on the denatured hemoglobin) is pooled, dialysed and lyophilised. This fraction elutes about where ovalbumin does i.e. 45,000 Doltens and contains about 15–20% of the applied proteolytic mixture.

2. Isoelectric focussing

The pooled, biologically active product from repeated G75 column runs is then subjected to isolectric focusing using a 0–40% succrose gradient contianing 1% LKB Ampholine in the LKB-8102 apparatus from pH 5 to 8 at 4° C. as described in the above identified patents. During elution, the absorbence of the various fractions at 280 mu was determined and the various fractions pooled, dialysed and assayed. Only the fraction at pH 6.4 demonstrated the dissecting activity (i.e. separating denatured from native tissue). If the G-75 fraction is dissolved in 4M urea as a solvent, it's isolectric point shifts from 6.4 to 6.8.

Repeated isoelectric focussing of this fraction gave a material absorbing u.v. at a peak of 280 mu which could dissect dead from live burned tissue to produce a graftable bed. This fraction was found to be electrophoretically homogenous at two different pH levels in acrylamide gel disc electrophoresis.

It is, of course, the same escharase isolated by the previously described procedures. It can dissect the plane between live and dead tissue but, has no general proteolytic activity against denatured hemoglobin, gelatin or casein. It also does not have hydrolytic activity against hyaluronic acid or dermatan sulfate, acid mucopolysaccharides of the skin.

Escharase is excluded from G-75 at a molecular weight of about 45,000 Daltons. After isoelectric focussing it appears to have a molecular weight on SDS-PAGE electrophoresis of about 15,000 and by Sephadex G-50 exclusion chromotagraphy of about 14,000 daltons. It therefor appears that Escharase is a complex of three identical subunits of about 15,000 Daltons which dissociate during isoelectric focussing.

The amino acid analysis of pure escharase is as follows:

| namomoles/nanomole of escharase (14,000 D) | |
|---|---|
| Alanine | 16 |
| arginine | 7 |
| aspartic acid | 12 |
| cystin/2 | 6.6 |
| glutamic acid | 10.6 |
| glycine | 16.8 |
| histidine | none |
| isoleucine | 6.4 |
| leucine | 6.4 |
| lysine | 5.6 |
| phenylalanine | 3.4 |
| proline | trace |
| serine | 14 |
| threonine | 7 |
| tyrosine | trace |
| vaLINE | 7.6 |
| methionine | none |
| Total | 115 nanomoles molecular weight of 13,800 |

Escharase then is essentially devoid of methionine, histidine, proline and tyrosine. The lack of proline and tyrosine indicates escharase is a unique protein.

The precipitated escharase containing proteolytic mixture is recovered, for example by centrifugation and may be purified and concentrated by lyophilization, if desired. For this purification procedure, the precipitated proteolytic mixture is dissolved in acetic acid and lyophilized up to, for example, five times.

The proteolytic mixture of this invention and the escharase derived from it will be utilized for the removal of eschar utilizing the same procedures described in the above identified patents and publication.

Variations from the procedures described, reagents and instruments specifically described will be apparent to those skilled in the art. Other types of filters may be employed. Any of a variety of proteins may be employed as standards in electrophoresis. Sucrose is not the only gradient which can be employed in the isoelectric focusing procedures. The exact details of these procedures may vary from the equivalent procedures described above.

What is claimed is:

1. A method for preparing a stable admixture of escharase and other proteolytic enzymes, said mixture being obtained by the steps comprising:
   (a) extracting bromelain having escharase activity with a dilute ascorbic acid solution at a pH of from about 3 to 4, thereby producing an aqueous extract containing non-denatured escharase and other proteolytic enzymes; followed by
   (b) precipitating the stable escharase and other proteolytic enzymes from the aqueous extract formed in step (a) at a pH of from about 3 to 4 with ammonium sulfate.

2. A method for preparing a stable admixture of escharase and other proteolytic enzymes, said mixture being obtained by the steps comprising:
   (a) extracting bromelain having escharase activity with a dilute aqueous antioxidant solution at a pH of from about 3 to 4, said solution containing ascorbic acid as an antioxidant, thereby producing an aqueous extract containing non-denatured escharase and other proteolytic enzymes; followed by
   (b) precipitating the escharase from the aqueous extract formed in step (a) at a pH of from about 3 to 4 by adding ammonium sulfate directly thereto.

* * * * *